US009869682B2

(12) United States Patent
Micallef et al.

(10) Patent No.: US 9,869,682 B2
(45) Date of Patent: Jan. 16, 2018

(54) METHOD FOR DETECTING THE PRESENCE OF A GYNAECOLOGICAL GROWTH

(71) Applicant: Singapore Volition Pte. Limited, Singapore (SG)

(72) Inventors: Jacob Vincent Micallef, London (GB); Mark Edward Eccleston, London (GB)

(73) Assignee: BELGIAN VOLITION SPRL, Isnes (BE)

( * ) Notice: Subject to any disclaimer, the term of this patent is extended or adjusted under 35 U.S.C. 154(b) by 167 days.

(21) Appl. No.: 14/842,430

(22) Filed: Sep. 1, 2015

(65) Prior Publication Data

US 2015/0369815 A1    Dec. 24, 2015

Related U.S. Application Data

(62) Division of application No. 13/811,813, filed as application No. PCT/GB2011/051354 on Jul. 19, 2011, now abandoned.

(30) Foreign Application Priority Data

Jul. 28, 2010 (GB) .................................. 1012662.1

(51) Int. Cl.
*G01N 33/68* (2006.01)
*G01N 33/53* (2006.01)

(52) U.S. Cl.
CPC .......... *G01N 33/689* (2013.01); *G01N 33/53* (2013.01); *G01N 33/6875* (2013.01); *G01N 2333/47* (2013.01); *G01N 2800/364* (2013.01)

(58) Field of Classification Search
None
See application file for complete search history.

(56) References Cited

U.S. PATENT DOCUMENTS

| 7,759,071 B2 | 7/2010 | Holdenrieder et al. |
| 2004/0220128 A1 | 11/2004 | Pavco et al. |
| 2007/0287676 A1 | 12/2007 | Guo et al. |
| 2013/0252245 A1 | 9/2013 | Micallef et al. |

FOREIGN PATENT DOCUMENTS

| WO | WO-99/47924 A1 | 9/1999 |
| WO | WO-01/62959 A2 | 8/2001 |

OTHER PUBLICATIONS

Abrao, et al., "The use of biochemical markers in the diagnosis of pelvic endometriosis", Human Reproduction vol. 12, No. 11, pp. 2523-2527, (1997).

Baldi, et al., "Endometriosis: Pathogenesis, diagnosis, therapy and association with cancer (Review)", Oncology Reports 19: 843-846, (2008).
D'Hooghe, et al., "Multi-disciplinary centres/networks of excellence for endometriosis management and research: a proposal", Human Reproduction vol. 21, No. 11, pp. 2743-2748, (2006).
D'Hooghe, et al., "Why We Need a Noninvasive Diagnostic Test for Minimal to Mild Endometriosiswith a High Sensitivity", Gynecol. Obstet. Invest., 62: pp. 136-138, (2006).
Flores, et al., "Molecular profiling of experimental endometriosis identified gene expression patterns in common with human disease", Fertil. Steril., 87(5): 1180-1199, (2007).
Hapangama, et al., "Sustained replication in endometrium of women with endometriosis occurswithout evoking a DNA damage response", Human Reproduction, vol. 24, No. 3 pp. 687-696, (2009).
Harsoulis, et al., "Combined Test for Assessment of Anterior Pituitary Function", British Medical Journal, 4, pp. 326-329, (1973).
Holdenrieder, et al., "Clinical use of circulating nucleosomes", Critical Reviews in Clinical Laboratory Sciences, 46(1): 1-24, (2009).
Holdenrieder, et al., "Nucleosomes in serum of patients with Benign and Malignant diseases", Int. J. Cancer (Pred. Oncol.): 95, 114-120 (2001).
Imai, et al., "Drastic elevation of serum CA125, CA72-4 and CA19-9 levels during menses in a patient with probable endometriosis", European Journal of Obstetrics & Gynecologyand Reproductive Biology 78: pp. 79-81, (1998).
International Search Report PCT/GB2011/051354 dated Aug. 11, 2011.
Kennedy, et al., "ESHRE guideline for the diagnosis and treatment of endometriosis", Human Reproduction vol. 20, No. 10 pp. 2698-2704, (2005).
Mclaren et al. Vascular endothilial growth factor (VEGF) concentrations are elevated in peritoneal fluid of women with endometriosis. Human Reproduction (1996) vol. 11, No. 1, pp. 220-223.
Mihalyi, et al., "Non-invasive diagnosis of endometriosis based on a combined analysis of six plasma biomarkers", Human Reproduction, vol. 25, No. 3 pp. 654-664, (Mar. 2010).
O'Shaughnessy, et al., "CA 125 Levels Measured in Different Phases of the Menstrual Cycle in Screening for Endometriosis", Obstet. Gynecol., vol. 81, No. 1, pp. 99-103, (1993).
Overton et al., "Atlas of Endometriosis, Third Edition (Encyclopedia of Visual Medicine Series)", Informa Healthcare, 2007.
Ponce, et al., "Nuclear factor KB pathway and interleukin-6 are affected in eutopic endometrium of women with endometriosis", Reproduction and Fertility, 137: 727-737, (2009).
Salgame, et al., "An ELISA for detection of apoptosis", Nucleic Acids Research, vol. 25, No. 3, pp. 680-681, (1997).
Seeber, et al., "Proteomic analysis of serum yields six candidate proteins that are differentially regulated in a subset of women with endometriosis", Fertility and Sterility, pp. 1-8, (2009).

(Continued)

*Primary Examiner* — David Thomas
(74) *Attorney, Agent, or Firm* — Foley & Lardner LLP (57) ABSTRACT

The invention relates to a method for detecting the presence of a gynaecological growth, in particular for the diagnosis of endometriosis. The invention also relates to a method of identifying a biomarker for detecting the presence of a gynaecological growth and to biomarkers identified by said method.

6 Claims, 1 Drawing Sheet

(56) References Cited

OTHER PUBLICATIONS

Signorile, et al., "Ectopic endometrium in human foetuses is a common event and sustains the theory of mullerianosis in the pathogenesis of endometriosis, a disease that predisposes to cancer", Journal of Experimental & Clinical Cancer Research, 28: 49, pp. 1-5, (2009).
Simoens, et al., "Endometriosis: cost estimates and methodological perspective", Human Reproduction Update, vol. 13, No. 4 pp. 395-404, (2007).
Templeman, Claire, "Adolescent Endometriosis", Obstet. Gynecol. Clin. N. Am., 36: pp. 177-185, (2009).
Van Nieuwenhuijze, et al., "Time between onset of apoptosis and release of nucleosomes from apoptotic cells: putative implications for systemic lupus erythematosus", Ann. Rheum. Dis., 62: pp. 10-14, (2003).
Wood, "Adenomyosis: Difficult to Diagnose, and Difficult to Treat", Diagnostic and Therapeutic Endoscopy, vol. 7, pp. 89-95, (2001).
Wood, et al., "Laparoscopic Surgical Techniques for Endometriosis and Adenomyosis", Diagnostic and Therapeutic Endoscopy, vol. 6, pp. 153-168, (2001).
Zachariah, et al., "Circulating cell-free DNA as a potential biomarker for minimal and mild endometriosis", RBM Online, vol. 18, No. 3, pp. 407-411, (2009).

METHOD FOR DETECTING THE PRESENCE OF A GYNAECOLOGICAL GROWTH

CROSS-REFERENCE TO RELATED APPLICATIONS

This application is a divisional of U.S. application Ser. No. 13/811,813 filed on Jun. 12, 2013, which is the U.S. national stage application of International Patent Application No. PCT/GB2011/051354, filed on Jul. 19, 2011, which claims priority to United Kingdom Application No. 1012662.1, filed on Jul. 28, 2010, each of which is incorporated herein by reference in its entirety.

FIELD OF THE INVENTION

The invention relates to a method for detecting the presence of a gynaecological growth, in particular for the diagnosis of endometriosis. The invention also relates to a method of identifying a biomarker for detecting the presence of a gynaecological growth and to biomarkers identified by said method.

BACKGROUND OF THE INVENTION

The incidence of endometriosis is not known accurately but is estimated at about 10% in women. Endometriosis is a significantly under-diagnosed and under-treated, disease. Diagnosis is usually made by visualization of endometriosis lesions by invasive surgery through laparoscopy or laparotomy with histological confirmation (Pasoto et al. 2008; Baidi et al, 2008).

Endometriosis is a benign gynaecological proliferative and inflammatory disease in which endometrial or endometrial-like tissue, which normally forms the uterine lining shed in menstruation, is present outside of its normal place in the uterus. Endometriosis growths occur most commonly in the pelvis, around the outside of the uterus, on the ovaries, the fallopian tubes, but are also found on the bowel, the bladder, the intestines, the vagina and the rectum. Endometriosis tissue may also occur in the muscle layer of the wall of the uterus (adenomyosis). Rarely, endometriosis tissue may grow in other areas including the skin, the eyes, the spine, the lungs and the brain. Although not a cancer, endometriosis has certain characteristics in common with benign tumours including progressive growth, invasive growth, oestrogen-dependent growth, recurrence and a tendency to metastasize (Van Gorp et al. 2004; Flores et al., 2007).

The normal endometrium lining of the uterus proliferates and thickens during the luteal phase of the menstrual cycle in response to rising circulatory levels of progesterone and estradiol. When the progesterone and estradiol levels fall at the end of the cycle (in the absence of fertilization) the endometrium breaks down and bleeds and is shed in menstruation, before re-growing when progesterone and estradiol levels rise again in the next cycle. Ectopic, endometriosis tissue is similarly influenced by the hormones of the menstrual cycle and grows and breaks down with bleeding. However, as this tissue is located outside of the uterus, the bleeding is internal with no way of leaving the body leading to inflammation, pain, and the formation of scar tissue (adhesions).

Symptoms of endometriosis may include pain, infertility, dysmenorrhoea and fatigue (D'Hooghe and Hummelshoj, 2006; D'hooghe of et al., 2006). The severity of the symptoms varies with the position of the endometriosis growths and the severity and stage of the disease. The severity may also increase with the total life-time number of menstrual cycles experienced by the patient. For this reason early diagnosis and early treatment to limit cycles is important. Endometriosis was thought to be rare in adolescents but is now more commonly diagnosed (Templeman, 2009). Under diagnosis or late diagnosis is common because endometriosis symptoms are non-specific and because many patients are asymptomatic. Endometriosis often remains undetected for a number of years.

The etiology of the disease is not known but a number of theories have been put forward. One theory involves anatomical or biochemical aberrations of uterine function; for example the implantation of menstrual tissue on pelvic organs following backwash of this tissue into the pelvis possibly due to vaginal blockage of outflow. Another theory involves small defects of embryogenesis in the foetus where endometrial-like tissue is developmental misplaced. Other theories involve the travel of menstrual tissue through veins or lymphatic, vessels to other sites or the differentiation of blood cells originating in the bone marrow into endometrial tissue at various sites (Bulun, 2009; Signorile et al., 2009).

Treatment of the disease is by removal of the endometriosis tissue surgically, often in the same operation in which diagnosis is made, or by the use of drugs including androgens (such as Danazol), GnRH agonists (such as Leuprolide, Burserelin, Goserelin or Nafarelin), progestagens (such as Gestrinone or Medroxyprogesterone) and oral contraceptives.

Diagnosis of endometriosis is currently made by inspection of the pelvis by laparoscopy. If growths are identified simultaneous treatment may foe performed (Kennedy et al., 2005). However, many patients with mild disease remain undiagnosed. There is a need for non-invasive or minimally invasive methods for endometriosis diagnosis to facilitate early treatment and to reduce the number of unnecessary laparoscopes performed (D'Hooghe et al, 2006; Kennedy, 2006).

Many methods for the diagnosis of endometriosis have been investigated but visualization of the lesions by invasive surgery through laparoscopy or laparotomy remains the method of choice with a clinical sensitivity, of approximately 98% and a clinical specificity of approximately 79% (Baldi et al, 2008; de Almeida Filho et al, 2008).

Biomarkers investigated as diagnostic tools for endometriosis include circulating DNA, the inflammatory cytokines interleukin (IL)-1, IL-6, and tumor necrosis factor $\alpha$, angiogenic factors, such as IL-8 and vascular endothelial growth factor and the tumour markers CA-125 and CA 19-9 (Seeber, 2009). Despite research to identify circulatory biomarkers for endometriosis, there is currently no clinically applicable blood test available for the detection of endometriosis (Zachariah et at, 2009; Seeber et al 2009).

As single biomarkers have proved ineffective to date as diagnostic fools in endometriosis, combinations of biomarkers that might together prove to foe diagnostic of the disease have been investigated. Serum concentrations of C-reactive protein and high sensitivity C-reactive protein are reported to foe of little use as a diagnostic tool for endometriosis (Lermann et al, 2009). Measurements of a combination of CCR1 mRNA in peripheral blood leukocytes and monocyte chemotactic protein-1 (MCP-1) and CA125 protein in serum has been investigated as a possible diagnostic test for endometriosis. The expression of CCR1 mRNA in peripheral blood leukocytes was measured by quantitative real-time polymerase chain reaction. MCP-1 and CA125 levels in serum were determined by ELISA and ECLIA. The method was reported to have a sensitivity of 92% and a specificity of 82% (Agic et al. 2008).

Mass spectrometry has been used to screen for proteins expressed differently in serum from patients with endometriosis versus normal controls, in one recent study three protein markers identified were measured to produce a sensitivity of 92%, and specificity of 75% (Zhang et al. 2009). In another study six proteins were measured to produce a test that identified approximately two thirds of endometriosis patients (Seeber, 2009).

Other minimally invasive methods investigated for the diagnosis of endometriosis include global gene analysis of the eutopic endometrium at late secretory phase (Sherwin et al, 2008) and patient response to preoperative hormonal therapy in terms of relief of chronic pelvic pain (Jenkins et al, 2008), but neither of these approaches has proved effective.

Elevated levels of circulating nucleosomes have been defected in the blood of some endometriosis patients outdo not discriminate between healthy and diseased subjects (Holdenrieder et al, 2001), Elevated levels of circulating DNA have also been detected in the blood, of some endometriosis patients and this has been investigated as a diagnostic measurement for the detection of endometriosis and found to have a clinical sensitivity of 70% and a clinical specificity of 87% (Zachariah et al, 2009, Zachariah et. al, 2008)

Two particular problems for blood assays of cell death products, including DNA (Zachariah et al, 2009) and nucleosomes (Holdenrieder et al, 2001), for use as diagnostic tools for the detection of endometriosis are that;
 (i) they have poor clinical sensitivity. Whilst elevated levels are found in some patients suffering with endometriosis, other patients with endometriosis do not have elevated levels. This leads to the misdiagnosis of many patients suffering with endometriosis as being disease free.
 (ii) they have poor clinical specificity. Whilst elevated levels are found in some patients suffering with endometriosis, elevated levels also occur in many other clinical conditions including malignant and benign tumours, autoimmune conditions, inflammatory conditions, and trauma. This means that not all positive results are due to endometriosis and the tests misdiagnose many patients with other conditions wrongly as suffering with endometriosis.

Similarly problems occur for the use of markers of inflammation, such as C-reactive protein, high sensitivity C-reactive protein, fibrinogen amyloid A and inflammatory cytokines such as IL-1, IL-6, IL-8 and tumour necrosis factor, soluble intercellular adhesion molecule or white blood cell count (Lermann et al, 2008). CA-125 has also been measured as a potential diagnostic marker for endometriosis and, although more often used as a tumour marker, is known to be associated with inflammation. These markers have been found to be raised in many, but not all, patients with endometriosis and may be raised in other conditions leading to low clinical sensitivity and specificity.

Due to these problems some workers in the field have tried to produce blood tests for endometriosis with improved clinical sensitivity and specificity following one or both of two broad strategies;
 (i) workers have measured combinations of a number of markers in the expectation that measurement of two or several or many different markers in the same patient would provide improved discrimination between patients with and without endometriosis. Recent examples of this approach include the measurement of CCR1 mRNA in peripheral blood leukocytes and monocyte chemotactic protein-1 (MCP-1) and CA125 protein in serum (Agic et al, 2008), a combination of three protein biomarkers (Zhang et al, 2009) and a combination of six protein biomarkers (Seeber 2009).
 (ii) workers have measured markers in samples taken at different phases within the menstrual cycle in the expectation that the discrimination provided by the marker level between patients with and without endometriosis may be improved by making the measurements in samples taken during a particular phase of the menstrual cycle, rather than samples taken at other phases or in untimed samples. A recent example of this approach involved the measurement of IL-1 receptor agonist in serum and peritoneal fluid in endometriosis patients during the proliferative and the secretory phases of the menstrual cycle, IL-1 receptor agonist was found to be lower in the peritoneal fluid of endometriosis patients than control patients but no such difference was found in serum. Moreover, no difference was found in the levels of IL-1 receptor agonist in samples taken during the secretory or proliferative phase of the menstrual cycle in either serum or peritoneal fluid samples (Zhang et al, 2007). This indicates that no advantage is gained by measurement of IL-1 receptor agonist in timed samples taken during a particular phase of the menstrual cycle.

Similarly, serum IL-12 and IL-18 levels were measured during the follicular and luteal phases of the menstrual cycle. IL-12 was raised in advanced endometriosis over control subjects but no such difference was observed for IL-18. Neither IL-12 nor IL-18 levels varied between the follicular and luteal phases of the menstrual cycle, either in endometriosis patients or in control subjects (Fairbanks et al. 2009).
 It has been reported that serum levels of CA-125, C-Reactive Protein, amyloid A, and anti-cardiolipin antibodies are on average elevated in endometriosis patients during Days 1-3 of the menstrual cycle (the first 3 days of menses). The levels of these markers were also measured during Days 8-10 of the menstrual cycle and were also elevated, but on average less elevated than during Days 1-3. Of these measurements serum CA-125 levels during Days 1-3 were reported to be the best predictor of advanced endometriosis although not for early disease. Clinical specificity was not determined as comparison was made with healthy patients and not tested, with patients suspected of having endometriosis but found to be disease free on laparoscopy (Abrao et al, 1997). This study was later extended to include the measurement of CA-15-3, CA-19-9, CEA, AFP and B2MG during Days 1-3 and 8-10. None of these additional markers were found to be discriminatory for endometriosis (Abrao et al, 1999) either during Days 1-3 or during Days 8-10.
 (iii) Some workers have combined the previous two approaches and measured multiple markers for endometriosis at different phases of the menstrual cycle in the expectation that measurement of multiple markers in the same patient would provide improved discrimination between patients with and without endometriosis and that this discrimination may be further improved by making those measurements in timed samples taken at a particular phase of the menstrual cycle. A recent example includes the measurement of six serum cytokines as predictors of endometriosis. The levels of three of these cytokines were found to be raised in endometriosis, over levels found in healthy patients. The best discriminator was found to be IL-6 measurement with sensitivity of 71% and specificity of 66%. Discrimination was not improved by the inclusion of other cytokine measurements. Measurements were taken during the proliferative and secretory phases of the menstrual cycle. No difference was found in the serum cytokine levels of any of the six markers when measured at different phases of the menstrual cycle. This indicates that no advantage is gained by measurement of multiple cytokines over IL-6 alone and that discrimination is not improved by making the measurements in samples taken during a particular phase of the menstrual cycle (Othman et al, 2008).

Another example of this approach involved the measurement of a plurality of biomarkers in samples taken morn patients in a determined phase of the menstrual cycle and the analysis of the concentrations found using a mathematical model to determine the presence or absence or degree of disease, in this approach the workers measured multiple biomarkers in samples taken during different phases (in particular the proliferative and secretory phases) of the menstrual cycle. The aim of this was to maximise disease discrimination by the inclusion of multiple biomarkers and measuring those biomarkers at the phase of the cycle where their individual and combined discrimination is maximised. The secretory phase was selected as the phase where the greatest discrimination was found and a computer programme was used to set multiple inter-dependent cutt-off points to maximise clinical sensitivity and specificity (WO 2008/049175).

None of these methods has been adopted in clinical practice and a non-invasive blood test for endometriosis remains a clear and unmet medical need (Zachariah et al, 2009; Seeber et al, 2000).

SUMMARY OF THE INVENTION

According to a first aspect of the invention there is provided a method for detecting the presence of a gynaecological growth which comprises the steps of:
(i) determining the day or phase of the menstrual cycle;
(ii) taking body fluid samples at two or more different times during the menstrual cycle, characterised in that a first sample is taken during the menses phase of the menstrual cycle and a second sample is taken during the luteal phase of the menstrual cycle;
(iii) measuring nucleosomes or a component part thereof in the body fluid samples; and
(iv) using the levels of nucleosome or a component part thereof in, and the difference in biomarker levels between, the two samples as an indicator of the presence of a gynaecological growth.

According to a second aspect of the invention there is provided a method for defecting the presence of a gynaecological growth which comprises the steps of:
(i) administering to a subject an exogenous hormone, or hormone analogue, or hormone agonist, or hormone antagonist or a drug or contraceptive steroid or other substance intended to induce a gynaecological response in a stimulation or repression test; and
(ii) measuring nucleosomes or a component part thereof in a body fluid; and (iii) determining whether the amount or nature of the nucleosomes or component part thereof present in the body fluid of the subject is altered by the administration of the said exogenous substance such that any cell death as detected by the release of nucleosomes or component part thereof, is associated with a gynaecological growth.

According to a third aspect of the invention there is provided a kit for diagnosing or monitoring endometriosis which comprises a ligand or binder specific for the nucleosome or component part thereof, or a structural/shape mimic of the nucleosome or component part thereof, together with instructions for use of the kit in accordance with any of the methods defined herein.

According to a fourth aspect of the invention there is provided a method for identifying a nucleosome component biomarker for detecting the presence of a gynaecological growth which comprises the steps of;
(i) determining the day or phase of the menstrual cycle;
(ii) taking body fluid samples at two or more different times during the menstrual cycle, characterised in that a first sample is taken during the menses phase of the menstrual cycle and a second sample is taken during either the follicular or luteal phase of the menstrual cycle;
(iii) measuring nucleosomes or a component part thereof in said first and second samples; and
(iv) determining whether the amount or nature of nucleosomes or component part thereof is controlled or influenced by the menstrual cycle, such that control or influence indicates the identity of a biomarker.

According to a fifth aspect of the invention there is provided a biomarker identified, by the method of the fourth aspect of the invention.

DETAILED DESCRIPTION OF THE INVENTION

According to a first aspect of the invention there is provided a method for detecting the presence of a gynaecological growth which comprises the steps of:
(i) determining the day or phase of the menstrual cycle;
(ii) taking body fluid samples at two or more different times during the menstrual cycle, characterised in that a first sample is taken during the menses phase of the menstrual cycle and a second sample is taken during the luteal phase of the menstrual cycle;
(iii) measuring nucleosomes or a component part thereof in the body fluid samples; and
(iv) using the levels of nucleosome or a component part thereof in, and the difference in biomarker levels between, the two samples as an indicator of the presence of a gynaecological growth.

Circulating nucleosomes are a biomarker of cell death (Holdenrieder and Stieber, 2009). It has been reported previously that some women with endometriosis have elevated levels of circulating nucleosomes (Holdenrieder et al 2001). There has been no investigation of whether these nucleosomes vary in level during different phases of the menstrual cycle. We have made serum measurements of circulating levels of intact nucleosomes in women not taking steroid drugs with endometriosis during the menses, follicular, peri-ovulatory and luteal phases of the menstrual cycle and compared these to similar measurements in women with no defected endometriosis by laparoscopy. Surprisingly nucleosome levels peak during the luteal phase of the menstrual cycle and are low during the menses when the endometrial cells die and are shed and inflammation peaks (Abrao et al 1997). The results are summarised in Table 1 and FIG. 1.

According to one particular aspect of the invention which may be mentioned, there is provided a method for detecting the presence of a gynaecological growth which comprises the steps of;
(i) determining the day or phase of the menstrual cycle;
(ii) taking body fluid samples at two or more different times during the menstrual cycle, characterised in that a first sample is taken during the menses phase of the menstrual cycle and a second sample is taken during either the secretory phase or the late proliferative phase of the menstrual cycle;
(iii) measuring a biomarker for cell death or destruction, apoptosis, cell growth or inflammation in the body fluid samples; and
(iv) using the biomarker levels in, and the difference in biomarker levels between, the two samples as an indicator of the presence of a gynaecological growth.

Previous reports on the use of biomarkers to detect endometriosis have focused on the discrimination of those biomarkers for endometriosis in samples taken at random, or in timed samples taken at a particular phase of the cycle, in most cases the levels of biomarkers are reported not to vary significantly when measured during different phases of the menstrual cycle, although some variation in CA-125 and C-Reactive Protein levels has been reported in samples taken during Days 1-3 and Days 8-10 of the menstrual cycle (Abrao et al, 1997). The data presented herein show that certain biomarkers for cell death and inflammation are not produced continuously during the menstrual cycle in endometriosis but are found in the blood during the luteal phase and are absent, or present at lower levels, during other phases of the menstrual cycle.

In one embodiment, said first sample is taken during Days 1-5 of the menstrual cycle and said second sample is taken during the period commencing Day 18 of the menstrual cycle and ending with the onset of menses in the subsequent menstrual cycle.

According to a further aspect of the invention, there is provided a method for detecting the presence of a gynaecological growth which comprises the steps of (i) measuring a biomarker for cell death, apoptosis or inflammation in a biological sample and (ii) demonstrating that the marker is associated with, caused by or emanates from the gynaecological growth wherever located in the body. According to a further aspect of the invention, there is provided a method for detecting the presence of a gynaecological growth which comprises the steps of (i) measuring a biomarker in a biological sample and (ii) demonstrating that the said marker is produced during a particular phase of the menstrual cycle but not at other times during the cycle, such that a gynaecological growth is indicated as the origin of the said biomarker.

According to a further aspect of the invention, there is provided a method for defecting the presence of a gynaecological growth which comprises the steps of (i) measuring a biomarker for cell death, apoptosis or inflammation in a biological sample and (ii) demonstrating that the said marker is produced during the luteal phase hut not at other times during the cycle, such that a gynaecological growth that degenerates causing cell death and/or inflammation during menses is indicated as the origin of the said biomarker.

It will be appreciated by those skilled in the art that biomarkers for cell death, apoptosis or inflammation are non-specific biomarkers and that high circulating levels of such biomarkers may indicate the presence of a number of other conditions (including for example; many cancers, autoimmune disorders or other inflammatory conditions). The present invention discriminates between subjects with high levels of these biomarkers due to endometriosis and subjects with high levels due to other disorders where the biomarker levels are not associated with a gynaecological growth and do not vary greatly during different phases of the menstrual cycle. This aspect provides the present invention with increased clinical specificity for endometriosis and thus overcomes one of the major disadvantages of previous methods for the defection of endometriosis—that many patients with other conditions are wrongly diagnosed as having endometriosis.

As the data presented herein show that these markers are produced by endometriosis-patients during certain times of the menstrual cycle and not at others, it will be appreciated by those skilled in the art, that measurement of biomarkers in samples taken at times when the biomarkers are not produced, either in samples taken at random or in timed samples, will fail to detect many patients with endometriosis. This aspect provides the present invention with increased clinical sensitivity for endometriosis and thus overcomes another of the major disadvantages of previous methods for the detection of endometriosis (that many patients with endometriosis are wrongly diagnosed as being disease free).

It will also be appreciated by those skilled in the art that dual measurement at times where the markers are present at maximal and minimal levels also increases the clinical sensitivity of the present invention further by detection of endometriosis in patients with mildly elevated or normal biomarker levels where these levels fall markedly during Day 10 and onwards. This aspect provides the present invention with improved clinical sensitivity (in addition to improved clinical specificity) over other methods involving measurement at Days 1-3 where mild endometriosis cannot be detected (Abrao et al, 1907).

According to a further aspect of the invention, there is provided a method for detecting the presence of a gynaecological growth which comprises the steps of (i) measuring a biomarker for cell death, apoptosis or inflammation in a biological sample and (ii) demonstrating that the amount or nature of said biomarker varies markedly during two or more different phases of the menstrual cycle, such that the difference in levels of said biomarker indicates the presence of a gynaecological growth that is susceptible to cell death and/or inflammation during menses.

In one embodiment of said first aspect of the invention said first sample is taken during Days 1-5 of the menstrual cycle and said second sample is taken during the period commencing Day 18 of the menstrual cycle and ending with the onset of menses in the subsequent menstrual cycle. Thus, according to a further aspect of the invention, there is provided a method for detecting the presence of a gynaecological growth which comprises the Steps of (i) measuring a biomarker for cell death, apoptosis or inflammation in a biological sample taken from a subject during Days 1 to 5 of the menstrual cycle and (ii) measuring the difference between the levels of the biomarker found in this sample and that found in another sample taken from the subject during Days 18 to 28, such that the variation in levels of said biomarker indicates the presence of a gynaecological growth that is susceptible to cell death and/or inflammation during menses.

In one embodiment of said first aspect of the invention said first sample is taken during the lime the subject is bleeding due to menstruation and said second sample is taken when the patient is not bleeding due to menstruation. Thus, according to a further aspect of the invention, there is provided a method for detecting the presence of a gynaecological growth which comprises the steps of (i) measuring a biomarker for cell death, apoptosis or inflammation in a biological sample taken from a subject when currently menstruating or bleeding and (ii) measuring the difference between the levels of the biomarker found in this sample and that found in another sample taken from the subject when not bleeding or menstruating, such that the variation in levels of said biomarker indicates the presence of a gynaecological growth that is susceptible to cell death and/or inflammation during menstruation.

In one embodiment, said nucleosome or component, pad thereof comprises an intact, nucleosome, a histone including a post-translationally modified histone, a histone variant or a nucleic acid including DNA or methylated DNA.

According to a further aspect of the invention, there is provided a method for detecting the presence of a gynaecological growth which comprises the steps of measuring a biomarker in samples taken during two different phases of the menstrual cycle and using the difference in the two measurements, either absolute or relative (for example a percentage change) as the indicator of the presence of endometriosis. Thus, for example the presence of a biomarker for cell death, apoptosis or inflammation (such as, for example, nucleosomes, DNA, C-Reactive Protein, CA-125 or interleukins) during menses which continues at an approximately continuous level during the different phases of the menstrual cycle indicates the absence of endometriosis whereas a changing level of biomarker during the different phases of the menstrual cycle beyond, a certain threshold indicates the presence of endometriosis in the patient.

According to a further aspect the invention involves the demonstration of the origin of a biomarker of cell death or inflammation as being associated with a gynaecological growth by determining whether the amount or nature of the biomarker is influenced by the administration of exogenous hormone, exogenous hormone analogue, hormone agonists hormone antagonists or a drug or contraceptive steroid or other substance intended to modify hormone activity in a stimulation or repression test. In such a test measurements of the biomarker are typically performed in a sample taken immediately before administration of the exogenous substance and then further measurements are made in samples taken at a specific time or times after administration to detect an effect, in one aspect the administration of exogenous substance would be aimed at stimulating a menses event and measuring a biomarker taken at a sample pre and post administration to determine if the menses stimulation was accompanied by an increase in biomarker. In another aspect the administration of exogenous substances would be aimed at the prevention or amelioration of a menses event and measuring a biomarker taken at a sample pre and post administration to determine if the prevention or amelioration of menses was accompanied by a decrease in the level of, or absence of, a biomarker compared to previous menses or expected levels, it will be clear to those skilled in the art that an advantage of this aspect is that the detection of endometriosis could be conducted in parallel with a treatment to prevent or ameliorate the symptoms of the gynaecological growth during menses.

Such hormones and drugs are known in the art and some are used in the treatment of endometriosis (Jenkins et al, 2008). In this aspect a difference in the biomarker level before and after administration of the exogenous substance indicates menstrual control of the biomarker and presence of endometriosis in the patient.

According to a further aspect of the invention, them is provided a method for identifying a biomarker for detecting the presence of a gynaecological growth which comprises the steps of (i) measuring a biomarker for cell death, apoptosis or inflammation in a biological sample and (ii) determining whether the amount or nature of said biomarker is controlled or influenced by menstrual hormones, such that control or influence of said biomarker indicates the identity of a biomarker.

According to a further aspect of the invention, there is provided a biomarker identified by the method as defined herein.

A further aspect of the invention provides ligands, such as naturally occurring or chemically synthesised compounds, capable of specific binding to the biomarker. A ligand according to the invention may comprise a peptide, an antibody or a fragment thereof, or a synthetic ligand such as a plastic antibody, or an aptamer or oligonucleotide; capable of specific binding to the biomarker. The antibody can be a monoclonal antibody or a fragment thereof capable of specific binding to the biomarker. A ligand according to the invention may be labeled with a detectable marker, such as a luminescent, fluorescent, enzyme or radioactive marker; alternatively or additionally a ligand according to the invention may be labelled with an affinity tag. e.g. a biotin, avidin streptavidin or His (e.g. hexa-His) tag.

A biosensor according to the invention may comprise the biomarker or a structural/shape mimic thereof capable of specific binding to an antibody against the biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to defect and/or quantify the biomarker. In these uses, the detection and/or quantification can be performed on a biological sample as defined herein.

Diagnostic or monitoring kits are provided for performing methods of the invention. Such kits will suitably comprise a ligand according to the invention, for detection and/or quantification of the biomarker, and/or a biosensor, and/or an array as described herein, optionally together with instructions for use of the kit.

A further aspect of the invention is a kit for detecting the presence of a gynaecological growth, comprising a biosensor capable of detecting and/or quantifying one or more of the biomarkers as defined herein.

Biomarkers for detecting the presence of a gynaecological growth are essential targets for discovery of novel targets and drug molecules that retard or halt progression of the disorder. As the level of the biomarker is indicative of disorder and of drug response, the biomarker is useful for identification of novel therapeutic compounds in m vitro and/or in vivo assays. Biomarkers of the invention can be employed in methods for screening for compounds that modulate the activity of the biomarker.

Thus, in a further aspect of the invention, there is provided the use of a ligand, as described, which can be a peptide, antibody or fragment thereof or aptamer or oligonucleotide according to the invention; or the use of a biosensor according to the invention, or an array according to the invention; or a kit according to the invention, to identify a substance capable of promoting and/or of suppressing the generation of the biomarker.

Also there, is provided a method of identifying a substance capable of promoting, or suppressing the generation of the biomarker in a subject, comprising administering a test substance to a subject animal and defecting and/or quantifying the level of the biomarker present in a test sample from the subject.

The term "biomarker" means a distinctive biological or biologically derived indicator of a process, event, or condition. Biomarkers can be used in methods of diagnosis, e.g. clinical screening, and prognosis assessment and in monitoring the results of therapy, identifying patients most likely to respond to a particular therapeutic treatment, drug screening add development. Biomarkers and uses thereof are valuable for identification of new drug treatments and for discovery of new targets for drug treatment.

It will be appreciated that the gynaecological growth may comprise any ectopic proliferative gynaecological disease in a human or animal subject. In one embodiment, said gynaecological growth comprises a benign or malignant gynaecological growth. In a further embodiment, said gynaecological growth comprises endometriosis in a human or animal subject.

Thus, according to a further aspect of the invention, there is provided a method of diagnosing endometriosis in a human or animal subject which comprises the steps of (i) measuring a biomarker for cell death, apoptosis, cell growth or inflammation in a biological sample and (ii) determining whether the amount or nature of said biomarker varies during the menstrual cycle, such that the variation of said biomarker indicates the diagnosis of endometriosis.

The terms "detecting" and "diagnosing" as used herein encompass identification, confirmation, and/or characterisation of a gynaecological growth. Methods, of defecting, monitoring of and of diagnosis according to the invention are useful to confirm the existence of a growth, to monitor development of the growth by assessing onset and progression, or to assess amelioration or regression of the growth. Methods of detecting, monitoring and of diagnosis are also useful in methods for assessment of clinical screening, prognosis, choice of therapy, evaluation of therapeutic benefit, i.e. for drug screening and drug development.

Efficient diagnosis and monitoring methods provide very powerful "patient solutions" with the potential for improved prognosis, by establishing the correct diagnosis, allowing rapid identification of the most appropriate treatment (thus lessening unnecessary exposure to harmful drug side effects), and reducing relapse rates.

In one embodiment, said biomarker is released from the cells of a gynaecological growth. Thus, according to a further aspect of the invention there is provided a method for the detection of a gynaecological growth which comprises the steps of (i) measuring a biomarker in a biological sample that is associated with or released from the cells of a gynaecological growth and (ii) demonstrating that the said biomarker is associated with menstruation, such that said biomarker indicates the presence of a gynaecological growth.

In one embodiment, step (ii) comprises determining whether the amount or nature of the biomarker is influenced by the administration of an exogenous substance, for example an exogenous hormone, hormone analogue, hormone agonist, hormone antagonist or a drug or other substances intended to modify hormone activity in a stimulation or repression test. In a further embodiment, said exogenous hormone comprises a contraceptive or other steroid, in one embodiment, multiple measurements of the biomarker are performed. In a further embodiment, said multiple measurements comprise measurements before, at or near the time of administration of the said exogenous substance.

One embodiment comprises determining the day or phase of the menstrual cycle at the time of measuring the biomarker. Thus, according to a further aspect of the invention there is provided a method for the detection of a gynaecological growth which comprises the steps of (i) determining the day or phase of the menstrual cycle and (ii) measuring a biomarker of cell death, apoptosis, cell growth or inflammation in a biological sample at said day or phase of the menstrual cycle.

In one embodiment, measurement of the biomarker is performed at a day or phase of the menstrual cycle in which low or high levels in the biological sample or nature of said biomarker are associated with the presence of a gynaecological growth. In a further embodiment, multiple measurements of the biomarker are performed on the same day or phase of multiple menstrual cycles. Comparisons may be made between the amount or nature of biomarker in samples taken on two or more occasions. Assessment of any change in the amount or nature of the biomarker in samples taken on two or more occasions may be performed. Modulation of the biomarker level is useful as an indicator of the state of the gynaecological growth. An increase in the level of the biomarker over time is indicative of onset or progression, i.e. worsening of the growth, whereas a decrease in the level of the biomarker indicates amelioration or remission of the growth, or vice versa. Such an embodiment provides the advantage of allowing the prognosis of the gynaecological growth to be predicted.

One particular embodiment which may be mentioned is wherein step (ii) comprises determining the day or phase of the menstrual cycle at the time of measuring the biomarker and performing multiple measurements of the biomarker at two or more days or phases in the menstrual cycle. Comparisons may be made between the samples taken on two or more occasions to assess whether changes to the amount and/or nature of the biomarker during the menstrual phases have occurred which indicate a gynaecological growth as the origin or cause of the biomarker.

According to a further aspect of the invention there is provided a method for the detection of a gynaecological growth which comprises the steps of (i) determining the days or phase of the menstrual cycle and (ii) measuring a biomarker of cell death, apoptosis, cell growth or inflammation in a biological sample taken during Days 18-28, and eliminating other possible causes of the presence of the biomarker such that endometriosis is left as the probable origin or cause of the said biomarker. Surprisingly this can be done on the basis of patient presentation and medical history for many subjects. For example, causes of high levels of biomarkers of cell death, other than endometriosis may be ruled unlikely on the basis of age, medical history and patient presentation. Elimination of trauma (for example; severe injury or surgery) can be eliminated by patient presentation and history. Extreme exercise (for example running a marathon) can be eliminated on patient history. Stroke and heart attack can be eliminated on patient presentation and history. Sepsis or other serious infection can be eliminated on patient presentation and other less common causes can similarly be eliminated as improbable causes of high biomarker levels of cell death in a suspected endometriosis patient. Thus it will be clear to those skilled in the art that measurement of a biomarker during menses, followed by active elimination of other possible causes of the presence of said biomarker may indicate that endometriosis is the most likely cause of the biomarker. In another aspect of the invention biomarkers of both cell death and inflammation are measured during menses and other causes of raised biomarkers for both cell death and inflammation are eliminated on the basis of patient age, presentation and history to leave endometriosis as the probable cause. In a further aspect, the invention comprises the steps of (i) measuring a biomarker of cell death, apoptosis, cell growth or inflammation in a biological sample taken during menses, (ii) eliminating other possible causes of the presence of the said biomarker indicating endometriosis as the probable origin and (iii) confirming endometriosis as the origin by laparoscopy. Those skilled in the art will appreciate that the advantage of this method will be to reduce the occurrence of unnecessary laparoscopic surgeries and that this is only possible where the clinical sensitivity of the method is high, that is to say that the proportion of women with endometriosis wrongly diagnosed as not having the disease is low.

It will be appreciated that the day or phase of the menstrual cycle can be determined in a number of ways known to the art. In one embodiment the step of determining the day or phase of the menstrual cycle is determined by reference to patient symptoms related to the menstrual cycle, such as temperature, pain and the onset or end of menstrual bleeding.

In an alternative embodiment, the step of determining the day or phase of the menstrual cycle is determined by measurement of menstrual hormones or metabolites. It will be appreciated that such hormones or metabolites may be measured in a body fluid, such as blood or urine. Such measurements are known in the art and include measurements of estradiol and other estrogens, progesterone, luteinising hormone, follicle stimulation hormone and hormone metabolites such as steroid glucuronides.

It is known that increased cell turnover, cell death and apoptosis lead to increased circulatory levels of markers such as cell free nucleosomes and cell free DNA (Holdenrieder et al, 2001; Swaminathan et al, 2006). Increased levels of circulating DNA and nucleosomes are found in the blood of endometriosis patients (Holdenrieder et al, 2001; Zachariah et al 2009). However, circulating cell free nucleosomes or DNA are non-specific indicators and occur in a wide variety of other diseases including inflammatory diseases, a large variety of benign and malignant conditions, autoimmune diseases, as well as following trauma or ischaemia (Holdenrieder et al 2001, Swaminathan et al, 2006).

In endometriosis the endometrial tissue outside of the uterus remains responsive to the menstrual cycle and proliferates and then breaks down leading to a cyclical inflammatory response. The data presented herein show that the cyclical growth and degeneration of the endometriosis tissue is associated with a variation in the blood levels of nucleosomes resulting from tissue turnover and/or from the associated inflammatory response. This aspect has not previously been investigated as a method for the detection of endometriosis. The cyclical growth and degeneration of the endometriosis tissue is also associated with a variation in the blood levels of biomarkers of inflammation resulting from tissue turnover and/or from the associated inflammatory response. This phenomenon has been observed previously (Abrao et al, 1997), but the difference in levels has not previously been used as a method for the detection of endometriosis.

In one embodiment, said biomarker comprises a biomarker of inflammation. Such markers of the inflammatory response are known in the art including, without limitation, C-reactive protein, high sensitivity C-reactive protein, fibrinogen, amyloid A, CA-125 and inflammatory cytokines such as IL-1, IL-6, IL-8 and tumour necrosis factor, soluble intercellular adhesion molecule, CA 125 or white blood cell count.

In one embodiment, said biomarker comprises a nucleosome. Nucleosomes form the fundamental repeating units of eukaryotic chromatin, which is used to pack the large eukaryotic genomes into the nucleus. The basic structure of the nucleosome includes nucleic acid bound to a complex of histone proteins including histones 1, 2, 3 and 4. References herein to nucleosomes include references to intact nucleosomes, any component part or parts of nucleosomes, epigenetically altered nucleosomes containing a histone containing a post-translational modification or nucleosomes containing a histone variant in one embodiment, said biomarker comprises an intact nucleosome or any component part or parts of a nucleosome.

In an alternative embodiment, said biomarker comprises a histone, post-translationally modified histone or histone variant. Histones are the chief protein components of chromatin. References herein to histones include references to a histone containing a post-translational modification. In one embodiment said biomarker comprises a histone containing a post-translational modification or an epigenetically altered nucleosome containing a histone containing a post-translational modification. In an alternative embodiment, said biomarker comprises a histone variant or a nucleosome containing a histone variant.

In an alternative embodiment, said biomarker comprises a nucleic acid. In a further embodiment, said nucleic acid is a nucleic acid of a specific sequence. In a further embodiment, said nucleic acid comprises DNA or RNA. In a yet further embodiment, said nucleic add comprises methylated DNA. In a further embodiment, said methylated DNA is circulating methylated DNA of a specific sequence.

In one embodiment the invention involves the measurement of circulating nucleosomes in the blood at a particular stage of the menstrual cycle at which the levels are predicted to be high or low. In a preferred embodiment the invention involves the measurement of circulating nucleosomes in blood taken during the phase of the menstrual cycle to coincide with a peak in cell death. These measurements have not previously been carried out in a timed manner. In an alternative embodiment the invention involves the measurement of circulating nucleic acids, such as DNA or RNA, in the blood at a particular stage of the menstrual cycle at which the levels are predicted to be high or low. In a preferred embodiment the invention involves the measurement of circulating nucleic-acids in blood taken during the phase of the menstrual cycle to coincide with a peak in cell death. These measurements have not previously been carried out in a timed manner.

In an alternative embodiment the invention involves the measurement of circulating nucleic acids, such as DNA or RNA, of specific sequences, in the blood at a particular stage of the menstrual cycle at which the levels are predicted to be high or low. In a preferred embodiment the invention involves the measurement of circulating nucleic acids of specific sequences in blood taken during the phase of the menstrual cycle to coincide with a peak in cell death. These measurements have not previously been carried out in a timed manner.

In an alternative embodiment the invention involves the measurement of circulating nucleic acids which have been altered epigenetically, such as methylated DNA, in the blood at a particular stage of the menstrual cycle at which the levels are predicted to be high or low. In a preferred embodiment the invention involves the measurement of circulating epigenetically altered nucleic acids in blood taken during the phase of the menstrual cycle to coincide with a peak in cell death. These measurements have not previously been carried out in a timed manner.

In an alternative embodiment the invention involves the measurement of circulating nucleic acids which have been altered epigenetically, such as methylated DNA, of specific sequences in the blood at a particular stage of the menstrual cycle at which the levels are predicted to be high or low, or the epigenetic modification of the nucleic acid is predicted to differ. In a preferred embodiment the invention involves the measurement of circulating epigenetically altered nucleic acids of specific sequences in blood taken during the phase of the menstrual cycle to coincide with a peak in cell death. These measurement's have not previously been carried out in a timed manner.

In an alternative embodiment, the invention involves the measurement of circulating histones which have been altered epigenetically through post translational modifications, or the measurement of nucleosomes containing such modified histones, in the blood at a particular stage of the menstrual cycle at which the levels are predicted to be high or low either in absolute terms or as a proportion of total nucleosomes. In a preferred embodiment the invention involves the measurement of circulating epigenetically altered histones or nucleosomes in blood taken during the phase of the menstrual cycle to coincide with a peak in cell death. These measurements have not previously been carried out in a timed manner.

In a preferred embodiment the invention involves the measurement of circulating nucleosomes in the blood at two or more stages of the menstrual cycle at which the levels are predicted to be high or low, thus demonstrating that the nucleosome blood levels are variable during the menstrual cycle. In a particularly preferred embodiment circulating nucleosomes are measured in two samples taken during the menses phase (Days 1-5) and during the luteal phase (Days 18-28) of the menstrual cycle, or in two samples taken during the follicular phase (Days 6-12) and during the luteal phase (Days 18-28) of the menstrual cycle. The difference in circulating nucleosome levels between the two samples reflecting the peak of cell death which later subsides is taken as an indication of the presence of endometriosis in the patient.

In an alternative embodiment the invention involves the measurement of a circulating biomarker of inflammation, such as C-reactive protein or other markers of inflammation as defined hereinbefore. In the blood at two or more stages of the menstrual cycle at which the levels are predicted to be high or low. Such an embodiment will therefore demonstrate that the inflammatory biomarker blood levels are variable during the menstrual cycle. In a preferred embodiment a circulating marker of inflammation is measured in two samples taken during the menses and during the luteal phase of the menstrual cycle. The difference in marker levels between the two samples is taken as an indication of the presence of endometriosis in the patient.

In an alternative embodiment the invention involves the measurement of circulating nucleic acids, such as DNA or RNA, in the blood at two or more stages of the menstrual cycle at which the levels are predicted to be high or low, thus demonstrating that the nucleic acid blood levels are variable under the influence of the menstrual cycle. In a preferred embodiment circulating nucleic acid is measured in two samples taken during the menses and during the luteal phase of the menstrual cycle, or in two samples taken during the follicular phase and during the luteal phase of the menstrual cycle. The difference in circulating nucleic acids levels between the two samples is taken as an indication of the presence of endometriosis in the patient.

In a further embodiment the invention involves the measurement of both a biomarker of cell death and a biomarker of inflammation, in the blood at two or more stages of the menstrual cycle at which the levels are predicted to be high or low, thus demonstrating that the biomarker levels are variable under the influence of the menstrual cycle. In a preferred embodiment circulating biomarkers are measured in two samples taken during the menses and during the luteal phase of the menstrual cycle, or in two samples taken during the follicular phase and during the luteal phase of the menstrual cycle. The difference in circulating biomarker levels between the two is taken as an indication of the presence of endometriosis in the patient. Measurement of both an inflammatory and a cell death biomarker in blood samples for the detection of endometriosis has not previously been investigated. It will be appreciated by those skilled in the art that an advantage of this embodiment is increased clinical sensitivity over previous methods due to the facility to detect growths associated with an increase in circulatory markers of cell death but not associated with an increase in circulatory markers of inflammation and vice versa. This may occur for example for a growth which exhibits cell death but is located in a position where this cell death causes minimal inflammation or for a growth which exhibits a large amount of inflammation for a minimal amount of cell death due to its location.

In an alternative embodiment the invention involves the measurement of circulating nucleic acids, such as DNA or RNA, of specific sequences in the blood at two or more stages of the menstrual cycle at which the levels are predicted to be high or low, thus demonstrating that the nucleic acid blood levels are variable under the influence of the menstrual cycle. In a preferred embodiment circulating nucleic acid of specific sequence is measured in two samples taken during the menses and during the luteal phase of the menstrual cycle, or in two samples taken during the follicular phase and during the luteal phase of the menstrual cycle. The difference in levels of circulating nucleic acids of specific sequence between the two samples is taken as an indication of the presence of endometriosis in the patient.

In an alternative embodiment the invention involves the measurement of circulating nucleic acids which have been altered epigenetically, such as methylated DNA, in the blood at two or more stages of the menstrual cycle at which the levels are predicted to be high or low either in absolute terms or relative to other nucleic acid levels, thus demonstrating that the nucleic acid blood levels are variable under the influence of the menstrual cycle. In a preferred embodiment epigenetically altered circulating nucleic acid is measured in two samples taken during the menses and during the luteal phase of the menstrual cycle, or in two samples taken during the follicular phase and during the luteal phase of the menstrual cycle. The difference in levels of epigenetically altered nucleic acids of specific sequence between the two samples is taken as an indication of the presence of endometriosis in the patient.

In an alternative embodiment the invention involves the measurement of circulating nucleic acids which have been altered epigenetically, such as methylated DNA, of specific sequences in the blood at two or more stages of the menstrual cycle at which the levels are predicted to be high or low either in absolute terms or relative to other nucleic acid levels, thus demonstrating that the nucleic acid blood levels, or the epigenetic modification of the nucleic add, are variable under the influence of the menstrual cycle. In a preferred embodiment epigenetically altered circulating nucleic acid of specific sequence is measured in two samples taken during the menses and during the luteal phase of the menstrual cycle, or in two samples taken during the follicular phase and during the luteal phase of the menstrual cycle. The difference in levels of epigenetically altered nucleic acids of specific sequence between the two samples is taken as an indication of the presence of endometriosis in the patient.

In an alternative embodiment the invention involves the measurement of circulating histones which have been altered epigenetically through post translational modifications of component histones, or the measurement of nucleosomes containing such modified histones, in the blood at two or more stages of the menstrual cycle at which the levels are predicted to be high or low either in absolute terms or as a proportion of total nucleosomes, thus demonstrating that the modified nucleosome or modified histone blood levels, or the nature of the modifications, are variable under the influence of the menstrual cycle. In a preferred embodiment epigenetically modified histones or nucleosomes are measured in two samples taken during the menses and during the luteal phase of the menstrual cycle, or in two samples taken during the follicular phase and during the luteal phase of the menstrual cycle. The difference in levels or nature of epigenetically modified histones or nucleosomes between the two samples is taken as an indication of the presence of endometriosis in the patient.

In one embodiment, blood nucleosome or nucleic acid levels, such as DNA or RNA, are measured after treatment with a hormone or other substance leading to an increase or decrease in the blood levels of nucleosomes or nucleic acids in patients with gynaecological growths. Such hormones, are known in the art and some are used in the treatment of endometriosis (Jenkins et al 2008).

In a further embodiment, blood nucleosome or nucleic acid levels, such as DNA, RNA and methylated DNA, are measured before and after treatment with a hormone leading to an increase or decrease the blood levels of nucleosomes or nucleic acids, thus demonstrating that the nucleosomes or nucleic add blood levels are variable under the influence of hormones. Such hormones are known in the art and some are used in the treatment of endometriosis (Jenkins et al, 2008).

In one embodiment, measurement of nucleosomes or modified nucleosomes or modified histones comprises an immunoassay. Such an immunoassay includes immunometric assays such as enzyme-immunometric assay (ELISA), fluorescence labelled immunometric assay, time-resolved fluorescence labelled immunometric assay, chemiluminescent immunometric assay, immunoturbidimetric assay, particulate labelled immunometric assay and immunoradiometric assay and competitive immunoassay methods including labelled antigen and labelled antibody competitive immunoassay methods with a variety of label types including radioactive, enzyme, fluorescent, time-resolved fluorescent and particulate labels, Western blots and other immunochemical assays. All of said immunoassay methods are well known in the ad, see for example Salgame et al, 1997 and van Nieuwenhuijze et al, 2003. A commercial kit for the immunometric (ELISA) measurement of nucleosomes has been used for measurement of nucleosomes in blood (Holdenrieder et al 2001).

Methods for the measurement of circulating nucleic acids in body fluids are well known in the art and include polymerase chain reaction (PCR) methods. See for example Swaminathan et al 2006 and Zaehariah et al, 2009.

In one embodiment, said biological sample comprises a body fluid. For example, biological samples that may be tested in a method of the invention include cerebrospinal fluid (CSF), whole blood, blood serum, plasma, menstrual blood, endometrial fluid, urine, saliva, or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner.

In one embodiment, the body fluid is blood, menstrual blood or a derivative of blood including serum and plasma or urine. In a further embodiment, the body fluid is blood. In a yet further embodiment said body fluid is menstrual blood. In an alternative embodiment, said body fluid is endometrial fluid.

In one embodiment, the method of the invention is repeated on multiple menstrual cycles. This embodiment provides the advantage of allowing the detection results to be monitored over a specified lime period. Such an arrangement will provide the benefit of monitoring or assessing the efficacy of treatment of the gynaecological growth. Such monitoring methods of the invention can be used to monitor onset, progression, stabilisation, amelioration, relapse and/or remission.

Thus, the invention also provides a method of monitoring efficacy of a therapy for a gynaecological growth in a subject, suspected of having such a growth, comprising detecting and/or quantifying the biomarker present in a biological sample from said subject. In monitoring methods, test samples may be taken on two or more occasions. The method may further comprise comparing the level of the biomarker(s) present in the test sample with one or more control(s) and/or with one or more previous test sample(s) taken earlier from the same test subject, e.g. prior to commencement of therapy, and/or from the same test subject at an earlier stage of therapy. The method may comprise detecting a change in trial nature or amount of the biomarker(s) in less, samples taken on different occasions.

Thus, according to a further aspect of the invention, there is provided a method for monitoring efficacy of therapy for endometriosis in a human or animal subject comprising:
  (a) quantifying the amount of the biomarker as defined herein; and
  (b) comparing the amount of said biomarker in a test sample with the amount present in one or more control(s) and/or one or more previous test sample(s) taken at an earlier time from the same test subject.

A decrease in the level of the biomarker in the test sample relative to the level in a previous test sample taken earlier from the same test subject is indicative of a beneficial effect, e.g. stabilisation or improvement, of said therapy on the disorder or suspected disorder. In a preferred embodiment the biomarker will be measured in repeat samples taken during the luteal phase (Days 18-28) of a plurality of menstrual cycles.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

Suitably, the time elapsed between taking samples from a subject undergoing defection or monitoring may be the menstrual cycle length of the subject or any multiple thereof. For subjects with a typical 4 week (28 day) cycle length this may be any one of 4, 8, 12, 18, 20, 24, 28, 32, 36, 40, 44, 48, 52 weeks or more. It will be appreciated by those skilled in the art that measurement during menses can also be effected by taking samples during subject menstruation or bleeding and that this may be the best method for patients with endometriosis who may have irregular menstrual cycles. Samples may be taken prior to and/or during and/or following endometriosis therapy. Samples can be taken at intervals over the remaining life, or a part thereof, of a subject.

Furthermore, once treatment has been completed, the method of the invention may be periodically repeated in order to monitor for the recurrence of the gynaecological growth.

In a further embodiment the monitoring of more rapid changes due to fast acting therapies may be conducted at shorter intervals of hours or days.

According to a further aspect of the invention, there is provided a method for identifying a biomarker for defecting the presence of a gynaecological growth which comprises the steps of (I) measuring a biomarker for cell death, apoptosis, cell growth or inflammation in a biological sample and (ii) determining whether the amount or nature of said biomarker varies during the menstrual hormones, such that control or influence of said biomarker indicates the identity of a biomarker.

The term "identifying" as used herein means confirming the presence of the biomarker present in the biological sample. Quantifying the amount of the biomarker present in a sample may include determining the concentration of the biomarker present in the sample. Identifying and/or quantifying may be performed directly on the sample, or indirectly on an extract therefrom, or on a dilution thereof.

In alternative aspects of the invention, the presence of the biomarker is assessed by defecting and/or quantifying antibody or fragments thereof capable of specific binding to the biomarker that are generated by the subject's body in response to the biomarker and thus are present in a biological sample from a subject having a gynaecological growth.

Identifying and/or quantifying can be performed by any method suitable to identify the presence and/or amount of a specific protein in a biological sample from a patient or a purification or extract of a biological sample or a dilution thereof, in methods of the invention, quantifying may be performed by measuring the concentration of the biomarker in the sample or samples. Biological samples that may be tested in a method of the invention include those as defined hereinbefore. The samples can be prepared, for example where appropriate diluted or concentrated, and stored in the usual manner.

Identification and/or quantification of biomarkers may be performed by defection of the biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 18, 17, 18, 19, or 20 amino acids in length.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g., aptamer, or oligonucleotide, capable of specifically binding the biomarker. The ligand may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (get filtration), ion exchange, affinity, HPLC, UPLC and other LC or LC MS-based techniques. Appropriate LC MS techniques include ICAT® (Applied Biosystems, CA, USA), or ITRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods of diagnosing or monitoring according to the invention may comprise analysing a sample of endometrial fluid by SELDI TOF or MALDI TOF to detect the presence or level of the biomarker. These methods are also suitable for clinical screening, prognosis, monitoring the results of therapy, identifying patients most likely to respond to a particular therapeutic treatment, for drug screening and development, and identification of new targets for drug treatment.

Identifying and/or quantifying the analyte biomarkers may be performed using an immunological method, involving an antibody, or a fragment thereof capable of specific binding to the biomarker. Suitable immunological methods include sandwich immunoassays, such as sandwich ELISA, in which the detection of the analyte biomarkers is performed using two antibodies which recognize different epitopes on a analyte biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic, particles, or Q-dots). Immunological methods may be performed, for example, in microtitre plate or strip format.

According to a further aspect of the invention, there is provided a biomarker identified by the method as defined herein.

In one embodiment, one or more of the biomarkers may be replaced by a molecule, or a measurable fragment of the molecule, found upstream or downstream of the biomarker in a biological pathway.

The identification of key biomarkers specific to a disease is central to integration of diagnostic procedures and therapeutic regimes. Using predictive biomarkers appropriate diagnostic tools such as biosensors can be developed; accordingly, in methods and uses of the invention, identifying and quantifying can be performed using a biosensor, microanalytical system, microengineered system, microseparation system, immunochromatography system or other suitable analytical devices. The biosensor may incorporate an immunological method for detection of the biomarker(s), electrical, thermal, magnetic, optical (e.g. hologram) or acoustic technologies. Using such biosensors, it is possible to detect the target biomarkers) at the anticipated concentrations found in biological samples.

As used herein, the term "biosensor" means anything capable of detecting the presence of the biomarker. Examples of biosensors are described herein.

Biosensors according to the invention may comprise a ligand or ligands, as described herein, capable of specific binding to the biomarker. Such biosensors are useful in defecting and/or quantifying a biomarker of the invention.

The biomarker(s) of the invention can be detected using a biosensor incorporating technologies based on "smart" holograms, or high frequency acoustic systems, such systems are particularly amenable to "bar code" or array configurations.

In smart hologram sensors (Smart Holograms Ltd. Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of one or more biomarkers of the invention combine biomolecular recognition with appropriate means to convert detection of the presence, or quantitation, of the biomarker in the sample info a signal. Biosensors can be adapted for "alternate site" diagnostic testing, e.g. in the ward, outpatients' department, surgery, home, field and workplace.

Biosensors to detect one or more biomarkers of the invention include acoustic, plasmon resonance, holographic and microengineered sensors, imprinted recognition elements, thin film transistor technology, magnetic acoustic resonator devices and other novel acousto-electrical systems may be employed in biosensors for detection of the one or more biomarkers of the invention.

Methods involving identification and/or quantification of one or more biomarkers of the invention can be performed on bench-top instruments, or can be incorporated onto disposable, diagnostic or monitoring platforms that can be used in a non-laboratory environment, e.g. in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-medicine.

Diagnostic kits for the diagnosis and monitoring of the presence of a gynaecological growth are described herein. In one embodiment, the kits additionally contain a biosensor capable of identifying and/or quantifying a biomarker. A kit for diagnosing or monitoring endometriosis is provided. Suitably a kit according to the invention may contain one or more components selected from the group: a ligand, or ligands specific for the biomarker or a structural/shape mimic of the biomarker, one or more controls, one or more reagents and one or more consumables; optionally together with instructions for use of the kit in accordance with any of the methods defined herein.

The identification of biomarkers for endometriosis permits integration of diagnostic procedures and therapeutic, regimes. Detection of a biomarker of the invention can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response, Biomarkers are useful in development of personalized therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, not achievable using the current measures.

Furthermore, diagnostic biomarker tests are useful to identify family members or patients with mild or asymptomatic endometriosis or who may be at high risk of developing symptomatic endometriosis. This permits initiation of appropriate therapy, or preventive measures, e.g. managing risk factors. These approaches are recognised to improve outcome and may prevent overt onset of the disorder.

Biomarker monitoring methods, biosensors and kits are also vital as patient monitoring tools, to enable the physician to determine whether relapse is due to worsening of the disorder, if pharmacological treatment is assessed to be inadequate, then therapy can be reinstated or increased; a change in therapy can be given if appropriate. As the biomarkers are sensitive to the state of the disorder, they provide an indication of the impact of drug therapy.

A regular healthy menstrual cycle is usually described as being an approximately monthly cycle designated as beginning at Day 0 with the onset of menses when the endometrial lining of the uterus is shed along with some blood. The menses phase typically lasts until Day 5 which marks the beginning of the proliferative phase. The proliferative phase involves a thickening of the endometrial lining of the uterus and continues until blood oestrogen, LH and FSH hormone levels peak and ovulation occurs on approximately Day 14. The formation of the corpus luteum marks the beginning of the secretory phase when progesterone levels rise and fall again typically by Day 28 in a healthy cycle, followed (in the absence of pregnancy) by onset of the subsequent menses.

The menstrual cycle is also alternatively described as comprising a menses, a follicular phase, a peri-ovulatory phase and a luteal phase. Menses occurs on approximately Days 1-5. The follicular phase involves the maturation of follicles in the ovary, it commences with the onset of menses and continues until blood oestrogen, LH and FSH hormone levels peak end ovulation occurs on approximately Day 14, The peri-ovulatory phase occurs approximately on days 14-17. The formation of the corpus luteum on approximately Day 14 marks the beginning of the luteal phase with rising progesterone levels and (in the absence of pregnancy) if ends in luteolysis with falling progesterone levels typically by Day 28 in a healthy cycle, followed by onset of the subsequent menses. It will be appreciated to those skilled in the art that the particular nomenclature used, for the menstrual cycle will not affect the implementation of the invention, in the present invention the menses phase is considered to begin at the onset of menstruation, usually considered Day 0 of the menstrual cycle, and to continue typically in a healthy subject until approximately Day 5. In one aspect of the invention measurement of a marker of cell death or inflammation produced in endometriosis patients during the menses period will be made in patient samples taken during the period from Day 0 to Day 5. It will be appreciated by those skilled in the art that (i) the length of menses may vary in individual patients and (ii) that the biomarker in the blood or other fluid sampled, produced by endometriosis patients, may not disappear immediate following the end of the phase, but may slowly fall over one, two, or a few days. Thus in some patients with irregular menstrual cycles or particularly long or short cycles, the phases may not correspond exactly to these days.

The invention will now be illustrated with reference to the following non-limiting examples.

Example 1

Serial serum or plasma samples are taken from a confirmed endometriosis and an endometriosis free patient on a number of days during the menstrual cycle and assayed for nucleosome levels using a nucleosome ELISA such as that described by Salgame et al, 1997, Holdenrieder et al, 2001 or van Nieuwenhuijze M et al, 2003. The day of the menstrual cycle on which each blood sample is taken is determined by reference to the onset or end of menstrual bleeding or by the measurement of menstrual hormones. The difference in nucleosome levels that occurs between the samples taken during menses and during the luteal phase for the endometriosis positive patient, but does not occur in the endometriosis negative patient is used as an indicator for the disease.

Example 2

Serial serum or plasma samples are taken from a confirmed endometriosis and an endometriosis free patient on a number of days during the menstrual cycle and assayed for DNA levels by PCR by the method of Zachariah et al, 2009. The day of the menstrual cycle on which each blood sample is taken is determined by reference to the onset or end of menstrual bleeding or by the measurement of menstrual hormones. The difference in DNA levels that, occurs between the samples taken during menses and during the luteal phases, for the endometriosis positive patient, but does not occur in the endometriosis negative patient is used as an indicator for the disease.

Example 3

Serial serum or plasma samples are taken from a confirmed endometriosis and an endometriosis free patient on a number of days during the menstrual cycle and assayed for C-Reactive Protein levels by an ELISA method. The day of the menstrual cycle on which each blood sample is taken is determined by reference to the onset or end of menstrual bleeding or by the measurement of menstrual hormones. The difference in C-Reactive Protein levels that occurs between the samples taken during menses and during the luteal phases for the endometriosis positive patient, but does not occur in the endometriosis negative patient is used as an indicator for the disease.

Example 4

Serial serum or plasma samples are taken from a confirmed endometriosis and an endometriosis free patient on a number of days during the menstrual cycle and assayed for CA-125 levels by an ELISA method. The day of the menstrual cycle on which each blood sample is taken is determined by reference to the onset or end of menstrual bleeding or by the measurement of menstrual hormones. The difference in CA-125 levels that occurs between the samples taken during menses and during the luteal phases for the endometriosis positive patient, but does not occur in the endometriosis negative patient is used as an indicator for the disease.

Example 5

Serum or plasma is taken from a number of confirmed endometriosis and endometriosis free patients and assayed for nucleosome levels using a nucleosome ELISA such as that described by Salgame et al, 1997, Holdenrieder et al, 2001 or van Nieuwenhuijze et al, 2003. The day of the menstrual cycle on which each subject was investigated is determined by reference to the onset or end of menstrual bleeding. It will be clear to those skilled in the art that this represents a cross-sectional study, rather than a longitudinal study, where a single sample taken at a variety of phases of the menstrual cycle is assayed from a number of patients. For the endometriosis positive samples there is an increase in the mean nucleosome levels for samples taken around the time of the luteal phase and lower levels for samples taken during other phases of the menstrual cycle. This difference does not occur or is much less pronounced for endometriosis free samples.

Figure 1:
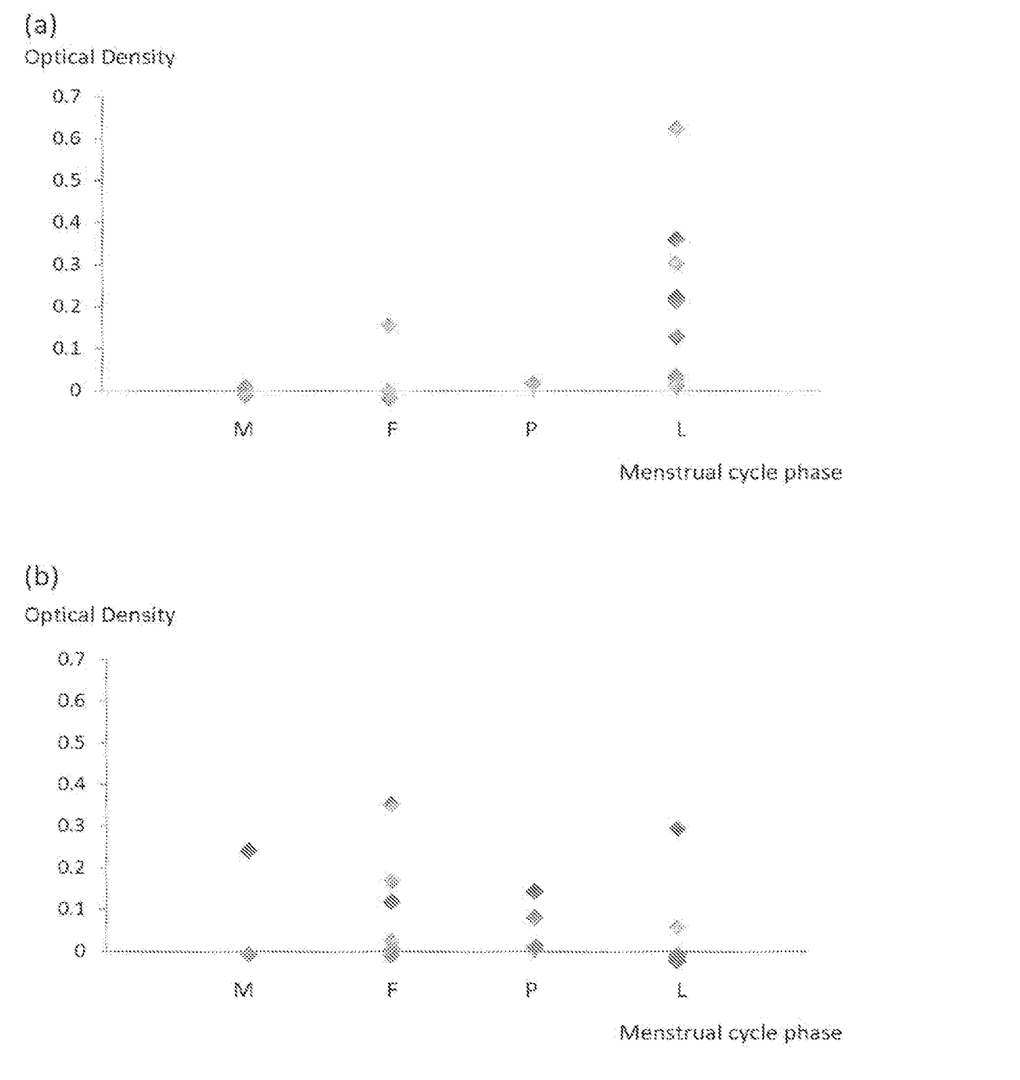
FIG. 1: Variation in circulating nucleosome levels during the menstrual cycle in (a) women with endometriosis and (b) women with no detectable endometriosis (arbitrary units). Legends refer to: M=menses, F=follicular phase, P=peri-ovulatory phase, L=luteal phase.

We coated microliter plates (Nunc F8 Maxisorp) with a mouse monoclonal anti-nucleosome antibody in 100 ul 0.1 M phosphate buffer pH 7.4 for 18 hours at 4° C. Excess antibody was removed by washing twice with 0.1 M phosphate buffer pH7.4 and wells were blocked by adding 200 ul 2% bovine serum albumin in 0.1M phosphate buffer pH7.4 and leaving at room temperature for 30 minutes. Excess bovine serum albumin was removed by washing three times with 200 ul 0.1M phosphate buffer pH7.4. To each well was added 10 ul of a serum sample from a defined phase of the menstrual cycle of a woman with or without endometriosis and 50 ul of assay buffer (0.05M TRIS/HCl pH 7.5 containing 0.9% w/v NaCl, 0.05% w/v sodium deoxycholate and 1% v/v Tween 20). Wells were incubated for 18 hours at 4° C. Serum was then decanted and removed by washing three times with 200 ul of wash buffer (0.05M TRIS/HCl pH 7.5 containing 1% v/v Tween 20). Biotinylated ante nucleosome antibody was added in assay buffer and incubated for 90 minutes at room temperature with shaking. Excess unbound biotinylated antibody was decanted and the wells again washed three times. Streptavidin-horse radish peroxidase conjugate was added in assay buffer and incubated for 30 minutes at room temperature with shaking. Excess unbound streptavidin conjugate was decanted and the wells again washed three times. Enzyme substrate (100 ul 2,2'-azino-bis(3-ethylbenzothiazoline-6-sulphonic acid) was added an incubated approximately 15 minutes with shaking and the colour produced was read on a plate reader at a wavelength of 405 nm. The colour intensity was used a measure of the level of nucleosomes present in the serum sample (arbitrary optical density units). The results are summarised in Table 1 and FIG. 1 show that the level of circulating nucleosomes present during the luteal phase is higher than during the menses and this effect is greater in women with endometriosis than women without endometriosis. Thus a large rise in nucleosome levels in the luteal phase over that present at the menses is indicative of endometriosis.

TABLE 1

Mean levels of circulating nucleosomes detected in women with and without endometriosis during menses and luteal phases (arbitrary units)

| Phase | Endometriosis positive | Endometriosis negative |
|---|---|---|
| Menses | undetectable | 0.12 |
| Luteal phase | 0.24 | 0.04 |

Example 6

Serum or plasma is taken from a number of confirmed endometriosis and endometriosis free patients and assayed for DNA levels by PCR by the method of Zachariah et al, 2009. The day of the menstrual cycle on which each subject was investigated is determined by reference to the onset or end of menstrual bleeding or by the measurement of menstrual hormones. It will be clear to those skilled in the art that this represents a cross-sectional study, where a single sample taken at a variety of phases of the menstrual cycle is assayed from a number of patients. For the endometriosis positive samples there is an increase in the mean DNA levels for samples taken around the time of the luteal phase and lower levels for samples taken during other phases of the menstrual cycle. This difference does not occur or is less pronounced for endometriosis free samples.

Example 7

Serum or plasma is taken from a number of confirmed endometriosis and endometriosis free patients and assayed for C-Reactive Protein levels by an ELISA method. The day of the menstrual cycle on which each subject was investigated is determined by reference to the onset or end of menstrual bleeding or by the measurement of menstrual hormones. It will be clear to those skilled in the art that this represents a cross-sectional study, where a single sample taken at a variety of phases of the menstrual cycle is assayed from a number of patients. For the endometriosis positive samples there is an increase in the mean for C-Reactive Protein levels for samples taken around the time of the menses and low levels for samples taken during the luteal phases of the menstrual cycle. This difference does not occur or is less pronounced for endometriosis free samples.

Example 8

Serum or plasma is taken from a subject on days from two different stages of the menstrual cycle and assayed for nucleosome levels using a nucleosome ELISA.

The days of the menstrual cycle on which the subject was investigated is determined by reference to the onset or end of menstrual bleeding or by the measurement of menstrual hormones. One of the samples is taken during the menses and the other is taken during the luteal phase of the menstrual cycle. If the difference in nucleosome levels that occurs between the samples taken during menses and during the luteal phases exceeds a preset cutoff the subject is considered positive for endometriosis, if the nucleosome levels measured are insufficiently different between the menses and the luteal phase and this difference does not exceed the cutoff, the subject is considered negative for endometriosis.

Example 9

Serum or plasma is taken from a subject on days from two different stages of the menstrual cycle and assayed for DNA levels by PCR by the method of Zachariah et al, 2009. The days of the menstrual cycle on which the subject was investigated is determined by reference to the onset or end of menstrual bleeding or by the measurement of menstrual hormones. One of the samples is taken during the menses and the other is taken during the luteal phase of the menstrual cycle. If the difference in DNA levels that occurs between the samples taken during menses and during the late proliferative or secretory phases exceeds a preset cutoff the subject is considered positive for endometriosis, if the DNA levels measured are insufficiently different between the menses and the luteal phase and this difference does not exceed the cutoff, the subject is considered negative for endometriosis.

Example 10

Serum or plasma is taken from a subject on days from two different stages of the menstrual cycle and assayed for C-Reactive Protein levels by an ELISA method. The days of the menstrual cycle on which the subject was investigated is determined by reference to the onset or end of menstrual bleeding or by the measurement of menstrual hormones, One of the samples is taken during the menses and the other is taken during the luteal phase of the menstrual cycle. If the difference in C-Reactive Protein levels that occurs between the samples taken during menses and during the luteal phases exceeds a preset cutoff the subject is considered positive for endometriosis. If the C-Reactive Protein levels measured are insufficiently and this difference does not exceed the cutoff, the subject is considered negative for endometriosis.

Example 11

Serum or plasma is taken from a subject previously diagnosed with endometriosis on a day of the menstrual cycle during menses which is predicted to be of high nucleosome levels and assayed for nucleosome levels using a nucleosome ELISA such as that described by Salgame et al, 1997, Holdenrieder et al, 2001 or van Nieuwenhuijze et al, 2003. The process is repeated on the same day of the menstrual cycle of subsequent menstrual cycles during treatment for the disease. The days of the menstrual cycle on which the subject was investigated is determined by reference to the onset or end of menstrual bleeding or by the measurement of menstrual hormones. The level of nucleosomes in the serum or plasma over time is used to monitor the efficacy of treatment, it will be appreciated by those skilled in the art that other biomarkers of cell death or inflammation including, without limitation, nucleic acids and C-Reactive Protein can be used in the same way to monitor efficacy of treatment.

Example 12

Serum or plasma is taken from a subject previously diagnosed with endometriosis on a day of the menstrual cycle during menses which is predicted to be of high nucleosome levels and assayed for nucleosome levels using a nucleosome ELISA. The process is repeated on the same day of the menstrual cycle of subsequent menstrual cycles. The days of the menstrual cycle on which the subject was investigated is determined by reference to the onset or end of menstrual bleeding or by the measurement of menstrual hormones. The level of nucleosomes in the serum or plasma over time is used to monitor the patient for the return of the disease. It will be appreciated by those skilled in the art that other biomarkers of cell death or inflammation including, without limitation, nucleic acids and C-Reactive Protein can be used in the same way to monitor for return of disease.

Example 13

A serum or plasma sample is taken from a confirmed endometriosis and a healthy patient on a day during the luteal phase of the menstrual cycle and assayed for nucleosome levels using a nucleosome ELISA such as that described by Salgame et al, 1997, Holdenrieder et al, 2001 or van Nieuwenhuijze et al 2003. The day of the menstrual cycle on which each blood sample is taken is determined by reference to the onset or end of menstrual bleeding or by the measurement of menstrual hormones, A high level of nucleosomes is found in the endometriosis positive patient and a lower level is found in the healthy patient it will be appreciated by those skilled in the art that other biomarkers of cell death or inflammation including, without limitation, nucleic acids and C-Reactive Protein can be used in the same way as an indicator of endometriosis provided the samples are taken at an appropriate time during the menstrual cycle when inflammation and cell death are occurring in endometriosis positive patients.

REFERENCES

Abrao et al Euro Soc Human Repro and Embry. 1997 12(11): 2523-2527
Abrao et al Int. J Gyn & Obs 1999 66:19-22
Agic et al Reprod Sci. 2008 November; 15(9):906-11;
Baldi et al Oncology Reports 2008 19: 843-846;
Bulun N Engl J Med 2009; 360; 268-79;
de Almeida Filho et al Sao Paulo Med J. 2008 November; 126(6):305-8;
D'Hooghe and Hummelshoj Human Reproduction 2008 Vol. 21, No. 11 pp. 2743-2748;
D'Hooghe et al Gynecol Obstet Invest. 2006; 62(3): 139-47;
Fairbanks et al Fertility and Sterility 2009 19(2) 320-324
Floras et al Fertil Steril. 2007 May; 87(5):1180-99.
Gao et al Curr Med Res Opin. 2006 September; 22(9):1787-97;
Holdenrieder and Stieber Critical Reviews in Clinical Laboratory Sciences, 2009; 46(1): 1-24:
Holdenrieder et at Int. J. Cancer (Pred. Oncol.), 2001; 95, 114-120 (2001):
Jenkins et al J Minim Invasive Gynecol. 2008 January-February; 15(1):82-6;
Kennedy Fertil Steril. 2006 November; 86(5):1296-301;
Kennedy et al Hum Reprod. 2005 October; 20(10):2698-704;
Lermann et at Fertil Steril. 2009 Feb. 14. [Epub ahead of print];
Othman et al European J Obstet & Gynecol and Reprod Biology, 2008, Vol. 137, 240-246
Pasoto et al 2008 Handbook of Systemic Autoimmune Diseases Vol. 9: 103-111
Salgame et al Nucleic Acids Research, 1997, Vol. 25, No. 3, 680-681;
Seeber et al Fertil Steril. 2009 Feb. 19. [Epub ahead of print];
Sherwin et al Hum Reprod. 2008 May; 23(5):1063-8;
Signorile et al J Exp & Clin Cancer Res. 2009 28:49;
Swaminathan and Butt Ann N Y Acad Sci. 2006 September; 1075:1-9:
Templeman C. Obstet Gynecol Clin North Am. 2009 March; 36(1): 177-85;
Van Gorp et al Best Pract Res Clin Obstet Gynaecol, 2004 April; 18(2):349-71:
van Nieuwenhuijze et al Ann Rheum Dis 2003; 62:10-14:
Zachariah et al Reproductive Bio Medicine Online; 2009; Vol 18 No 3, 407-411;
Zachariah et al Obstetrics & Gynaecology; 2008: Vol 112 No 4, 843-850
Zhang et al Chin Med J (Engl). 2009 Feb. 20; 122(4):373-6.
Zheng et al Fertility and Sterility, 2007, Vol 88, No. 3, 594-599

The invention claimed is:

1. A method of treating endometriosis in a subject in need thereof, wherein the endometriosis results from a gynaecological growth, which method comprises the steps of:
   (i) determining the day or phase of the subject's menstrual cycle;
   (ii) taking body fluid samples at two or more different times during the menstrual cycle, characterised in that a first sample is taken during the menses phase of the menstrual cycle and a second sample is taken during either the follicular or luteal phase of the menstrual cycle, wherein the body fluid sample is blood;
   (iii) measuring intact nucleosome biomarkers in said first and second samples;
   (iv) using levels of the intact nucleosomes in the two samples, and the difference in the biomarker levels between the two samples, as an indicator of the presence of the gynaecological growth; and
   (v) removing the gynaecological growth surgically, or administering to the subject in need thereof a pharmaceutical composition comprising one or more of androgens, GnRH agonists, progestagens, and oral contraceptives, thereby treating endometriosis.

2. The method of claim 1, wherein the second sample is taken during the follicular phase of the menstrual cycle.

3. A method as defined in claim 1, wherein said biomarker is released from the cells of the gynaecological growth.

4. A method as defined in claim 1, wherein the step of determining the day or phase of the menstrual cycle is determined by reference to patient symptoms related to the menstrual cycle, such as temperature, pain and the onset or end of menstrual bleeding.

5. A method as defined in claim 1, wherein the step of determining the day or phase of the menstrual cycle is determined by measurement of menstrual hormones or metabolites.

6. A method as defined in claim 1, which is repeated on multiple menstrual cycles.

* * * * *